(12) United States Patent
Baumfalk et al.

(10) Patent No.: US 8,822,210 B2
(45) Date of Patent: Sep. 2, 2014

(54) INCUBATOR COMPRISING A SHAKING DEVICE

(75) Inventors: Reinhard Baumfalk, Goettingen (DE); Stefan Obermann, Adelebsen-Erbsen (DE); Rainer Sandrock, Kassel (DE)

(73) Assignee: Sartorius Stedim Biotech GmbH (DE)

( * ) Notice: Subject to any disclaimer, the term of this patent is extended or adjusted under 35 U.S.C. 154(b) by 429 days.

(21) Appl. No.: 12/867,499

(22) PCT Filed: Feb. 17, 2009

(86) PCT No.: PCT/EP2009/001089
§ 371 (c)(1),
(2), (4) Date: Aug. 13, 2010

(87) PCT Pub. No.: WO2009/106248
PCT Pub. Date: Sep. 3, 2009

(65) Prior Publication Data
US 2010/0330663 A1      Dec. 30, 2010

(30) Foreign Application Priority Data
Feb. 25, 2008   (DE) .......................... 10 2008 010 780

(51) Int. Cl.
*C12M 3/00*         (2006.01)
*B01F 11/00*       (2006.01)
*C12M 1/00*        (2006.01)
*C12M 1/02*        (2006.01)
*C12M 3/06*        (2006.01)

(52) U.S. Cl.
CPC ............... *C12M 23/50* (2013.01); *C12M 23/48* (2013.01); *C12M 27/00* (2013.01); *C12M 27/16* (2013.01); *B01F 11/00* (2013.01); *B01F 11/0008* (2013.01); *B01F 11/0014* (2013.01); *B01F 11/0094* (2013.01); *Y10S 435/809* (2013.01)

USPC .................. 435/303.3; 435/303.1; 435/304.1; 435/305.1; 435/809; 366/128; 366/111; 366/112; 366/114; 366/115

(58) Field of Classification Search
CPC ...... C12M 27/16; C12M 23/48; C12M 23/50; B01F 11/00; B01F 11/0008; B01F 11/0014; B01F 11/0094
USPC ............. 435/303.3, 303.1, 304.1, 305.1, 809; 366/128, 111, 112, 114, 115
See application file for complete search history.

(56) References Cited

U.S. PATENT DOCUMENTS 3,601,372 A    8/1971   Harmes, III
5,558,437 A *  9/1996   Rode ............................. 366/208

(Continued)

FOREIGN PATENT DOCUMENTS

DE         198 14 013         7/1999
DE      10 2004 052 156       5/2006

(Continued)

*Primary Examiner* — Nathan Bowers
(74) *Attorney, Agent, or Firm* — Gerald E. Hespos; Michael J. Porco; Matthew T. Hespos

(57) ABSTRACT

An incubator (1) has an incubation chamber (2) and a shaking device (4) to shake receptacles (5) placed in the incubation chamber (2). A device chamber (3) adjoins the incubation chamber (2) and accommodates at least parts of the shaking device (4). The shaking device (4) has a base plate (8) that seals off the incubation chamber (2) from the device chamber 3. A shaking table (11) is on the inner face (9) of the base plate (8) and can be moved in a horizontal plane by a drive arm (10). A motor (34) is arranged on the outer face (37) of the base plate (8). The motor (34) drives a drive shaft (14) that is rotatably mounted in the base plate (8) and that is operatively connected to the drive arm (10).

11 Claims, 2 Drawing Sheets

(56) References Cited

U.S. PATENT DOCUMENTS

| | | | |
|---|---|---|---|
| 5,577,837 A | 11/1996 | Martin et al. | |
| 5,958,763 A * | 9/1999 | Goffe | 435/303.1 |
| 6,106,143 A | 8/2000 | Nickel et al. | |
| 6,881,572 B2 * | 4/2005 | Fitzgerald et al. | 435/303.3 |
| 2002/0055166 A1* | 5/2002 | Cannon et al. | 435/286.5 |
| 2006/0035368 A1* | 2/2006 | Malinge | 435/286.2 |
| 2008/0299652 A1* | 12/2008 | Owen et al. | 435/303.3 |
| 2009/0225626 A1 | 9/2009 | Baumfalk et al. | |

FOREIGN PATENT DOCUMENTS

| | | |
|---|---|---|
| DE | 20 2007 005 865 | 8/2007 |
| EP | 1 626 082 | 2/2006 |
| EP | 1 854 871 | 11/2007 |
| WO | 02/010100 | 12/2002 |

* cited by examiner

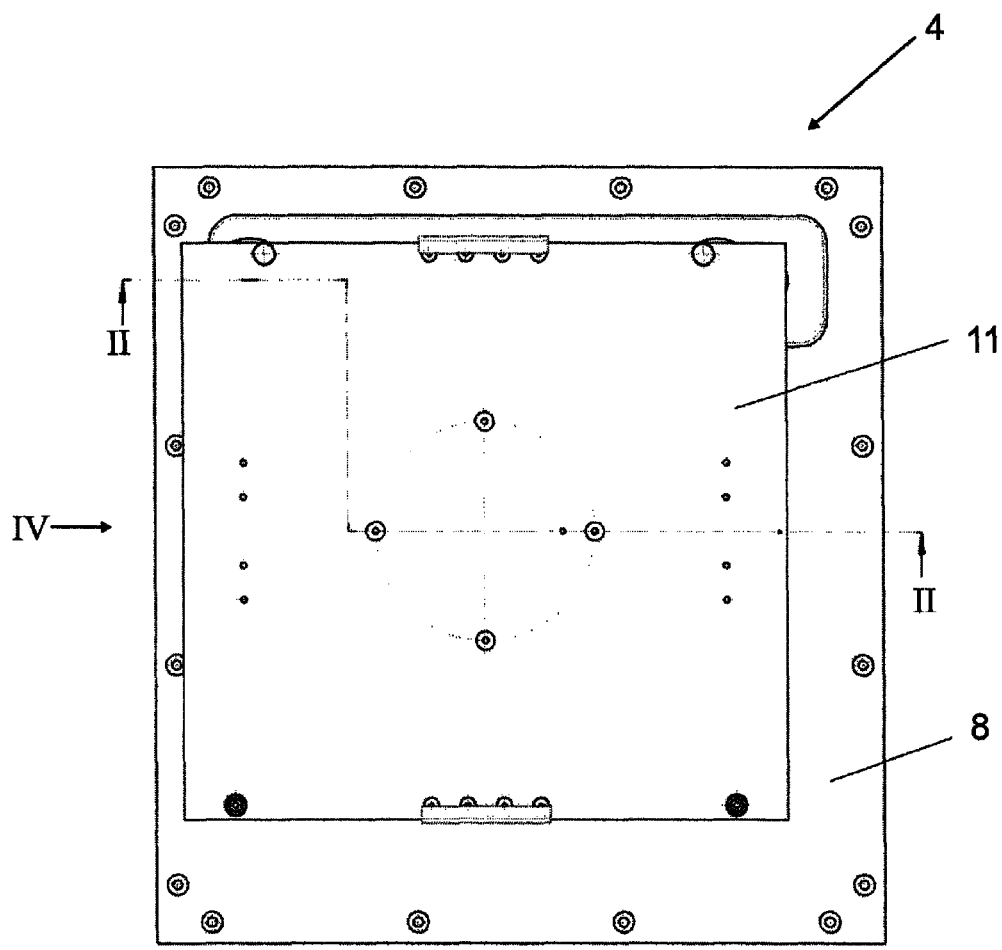
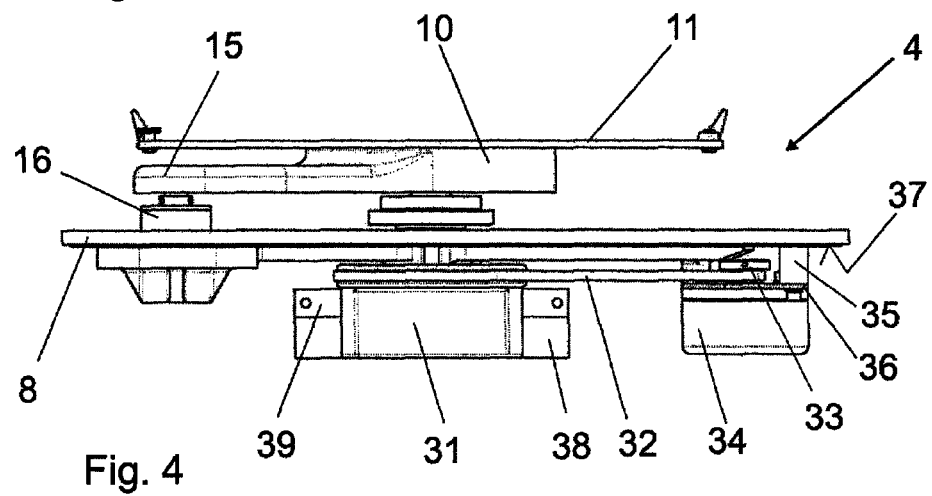

INCUBATOR COMPRISING A SHAKING DEVICE

BACKGROUND OF THE INVENTION

1. Field of the Invention

The invention relates to an incubator with an incubation chamber, a shaking device which can be driven by a drive unit and which is used to shake receptacles that can be placed in the incubation chamber and that contain cell cultures, and a device chamber which adjoins the incubation chamber and which accommodates at least parts of the shaking device protruding into the incubation chamber.

2. Description of the Related Art

Incubators are used to cultivate cell cultures that are arranged in receptacles placed in the incubation chamber. Shaking devices are used in order to achieve better cell growth.

EP 1 626 082 B1 discloses an incubator comprising an incubation chamber at whose lower end a device chamber is arranged. The device chamber accommodates a shaking device for shaking or agitating receptacles that are placed in the incubation chamber and that hold cell cultures. For this purpose, a shaft protrudes into the incubation chamber and has, at its free end, a shaking table for receiving the receptacles. The shaft extending into the incubation chamber has to rotate and also has to execute eccentric reciprocating movements in a horizontal plane.

A disadvantage of the above is that, because of the shaking movement, the seal between incubation chamber and device chamber can be provided only via an elastic bellows. Bellows of this kind are susceptible to wear and can, for example, tear, such that moisture from the incubation chamber can enter the device chamber. Moreover, the heat generated in the device chamber, particularly by the motor of the shaking device, can affect the climate in the incubation chamber by way of the bellows.

Moreover, DE 198 14 013 C1 discloses a shaking device which is arranged in its entirety in an incubation chamber of an incubator.

A disadvantage of this known device is that the heat given off by the device can affect the climate in the incubation chamber in an undesirable manner. In this device too, moisture from the incubation chamber can enter the shaking device.

Moreover, DE 20 2007 005 865 U1 discloses an incubator with an incubation chamber in which a shaking device is arranged. In this device, the problem of the heat given off by the shaking device and entering the incubation chamber is solved by a coolant circuit. The coolant circuit is not needed for the culturing, and to provide it simply to take up the heat given off by the shaking device is therefore relatively expensive and complicated.

The object of the present invention is therefore to make available an incubator with a shaking device in which the climate in the incubation chamber is largely unaffected by heat introduced by the shaking device. The shaking device should at the same time be protected as much as possible from the moisture in the incubation chamber.

SUMMARY OF THE INVENTION

The object is achieved by the fact that the shaking device has a base plate which seals off the incubation chamber relative to the device chamber and which, on its inner face directed toward the incubation chamber, has a shaking table that can be moved in a horizontal plane by a drive arm. A motor is arranged on the outer face of the base plate directed away from the inner face. The motor drives a drive shaft that is rotatably mounted in the base plate and that is operatively connected to the drive arm.

By arranging the motor on the outer face of the base plate and arranging the drive arm with the movable shaking table on the inner face of the base plate, it is possible to mount the drive shaft on the base plate rotatably but fixedly, i.e. without superposed sideways movements. It is thus possible to dispense with a bellows and to achieve an effective seal of the incubation chamber relative to the device chamber by way of the base plate. It is thereby possible in practice to avoid heat from the device chamber entering the incubation chamber. It is also possible to avoid moisture from the incubation chamber entering the device chamber. The shaking movements of the shaking table movable in a horizontal plane are generated on the inner face of the base plate directed toward the incubation chamber. The shaking device can be fitted relatively simply and inexpensive as an insert device by fixing the base plate between incubation chamber and device chamber.

According to a preferred embodiment of the invention, the drive shaft, at its end directed toward the device chamber, has a flywheel disk that can be driven by the motor. The flywheel disk is arranged centrally on a lower axle journal and is connected by a drive belt to a drive wheel of the motor. A radially displaceable counterweight is arranged on the flywheel disk. A centrifugal force generated by the weight that is to be shaken can be compensated by the counterweight.

According to another preferred embodiment of the invention, the drive shaft, at its end directed toward the incubation chamber, i.e. on the inner face of the base plate, has an eccentric piece with an upper axle journal, which is arranged parallel and offset in relation to the lower axle journal. The drive shaft is thus connected to the drive arm via the eccentric piece. The drive arm is additionally mounted, with two radially protruding ends, on the base plate via in each case an eccentric rotary joint. By rotation of the drive shaft, therefore, the drive arm is set in shaking movements in eccentric paths in a plane lying transverse to the longitudinal axis of the drive shaft. In order to avoid vibrations, the eccentric rotary joints each have an elastic damping member.

According to another preferred embodiment of the invention, the drive shaft is connected to the base plate via two ball bearings arranged one above the other. However, it is also possible in principle to use only one ball bearing or roller bearing or also another slide bearing.

According to another preferred embodiment of the invention, a seal is arranged between the drive shaft and the base plate. The seal is designed, for example, as a low-friction lip seal or labyrinth seal. This avoids moisture from the incubation chamber entering the device chamber.

Further features of the invention will become clear from the following detailed description and from the attached drawings in which preferred embodiments of the invention are illustrated by way of example.

BRIEF DESCRIPTION OF THE DRAWINGS

FIG. 3 shows a plan view of the shaking device from FIG. 2.

FIG. 4 shows a side view of the shaking device from direction IV in FIG. 3.

DETAILED DESCRIPTION OF THE PREFERRED EMBODIMENTS

Figure 1:
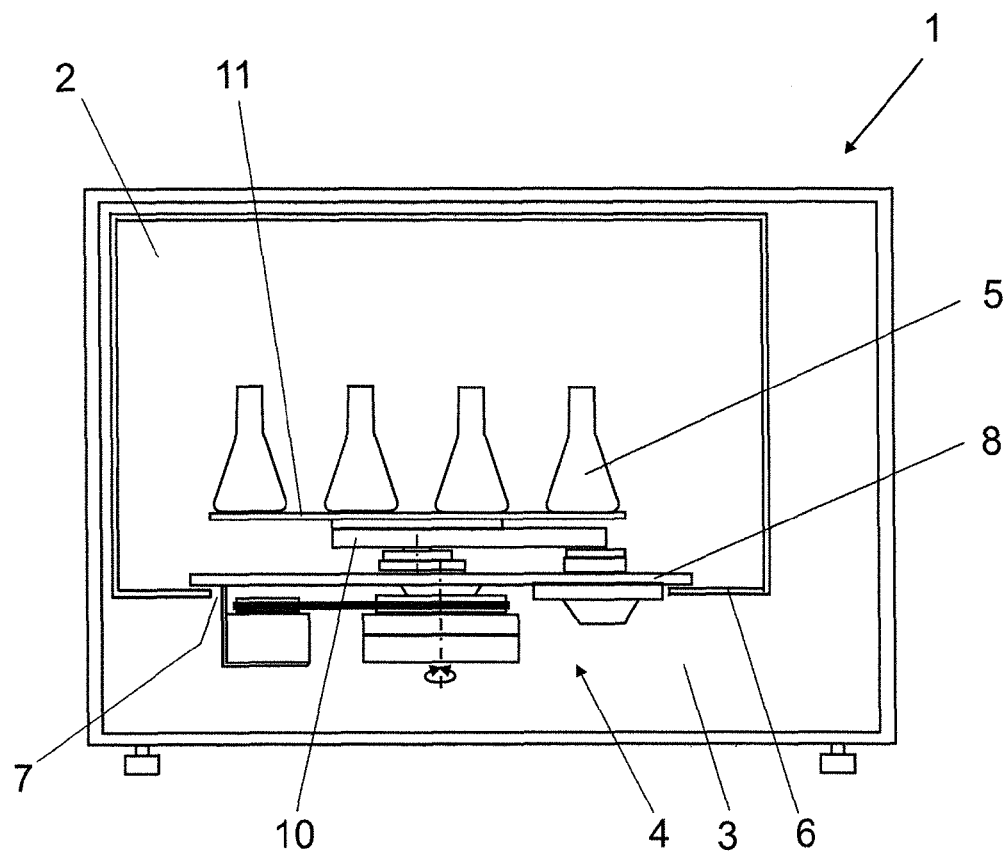
FIG. 1 shows a schematic side view of an incubator with a shaking device.
Figure 2:
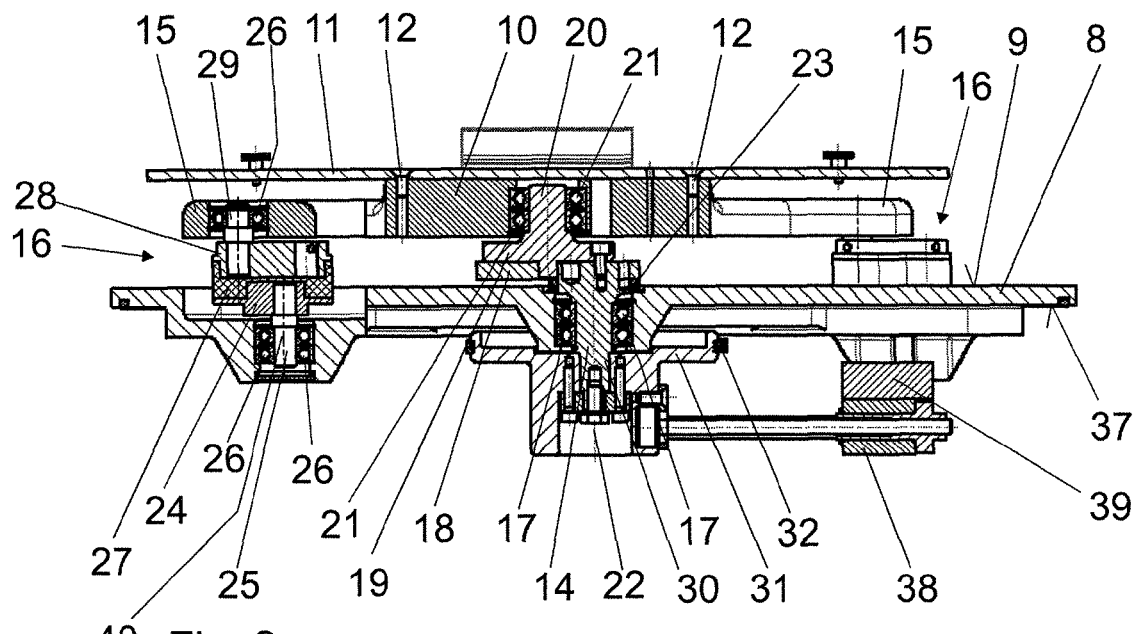
FIG. 2 shows a side view of a shaking device in section along the line II-II from FIG. 3.

An incubator 1 basically comprises an incubation chamber 2, a device chamber 3 and a shaking device 4.

The incubation chamber 2, in which cell cultures placed in receptacles 5 are cultivated, is arranged in the incubator 1. For the purpose of cultivation, the temperature and humidity in the incubation chamber 2 can be adjusted. A device chamber 3 is arranged vertically below the incubation chamber 2. A floor 6 of the incubation chamber 2 has, toward the device chamber 3, a floor opening 7 that serves as a connection to the device chamber 3.

The shaking device 4 is designed as an insert device which can be fitted into the floor opening 7 in such a way that the base plate 8 of the device seals off the incubation chamber 2 relative to the device chamber 3. On its inner face 9 directed toward the incubation chamber 2, the base plate 8 has a shaking table 11 that can be moved in a horizontal plane by a drive arm 10. The shaking table 11 is connected securely to the drive arm 10 by screws 12. The drive arm 10 is connected, on the one hand, to a drive shaft 14 via an axle journal 20 and, on the other hand, to the base plate 8 via two eccentric rotary joints 16 arranged at radially protruding ends 15 of the drive arm 10 and via the joint pins 25 and 29 of said rotary joints 16.

The drive shaft 14 is mounted on the base plate 8 via two successive groove and ball bearings 17. At its upper end in the vertical direction, the drive shaft 14 has a receiving seat 18 for the axle journal 20. At its lower end, the axle journal 20 has a flange 19, with which it can be screwed onto the receiving seat 18. At the top in the vertical direction, the upper axle journal 20 is mounted rotatably in the drive arm 10 via two ball bearings 21. The upper axle journal 20 is arranged laterally offset and parallel to the longitudinal axis 22 of the drive shaft 14. With its flange 19, the axle journal 20 can be secured on the receiving seat 18 of the drive shaft 14 at at least two different distances from the longitudinal axis 22. The drive shaft 14 is sealed off from the base plate 8 by a seal 23 on the inner face 9.

The rotary joints 16 have a lower joint part 24 with a lower joint pin 25, via which they are mounted rotatably on the base plate 8 by ball bearings 26. By way of an elastic damping member 27, the lower joint part 24 is connected to an upper joint part 28, which has an upper joint pin 29 mounted rotatably in turn in the drive arm 10 via a ball bearing 26.

The upper joint pin 29 can be secured on the upper joint part 28 at at least two different distances from the longitudinal axis 40 of the lower joint pin 25. This distance corresponds to the lateral distance of the upper axle journal 20 from the longitudinal axis 22 of the drive shaft 14.

At its end directed toward the device chamber 3, the drive shaft 14 has a lower axle journal 30 on which a flywheel disk 31 is arranged, which is connected by a drive belt 32 to a drive wheel 33 of a motor 34 that drives the shaking device 4. By way of support columns 35, the motor 34 is mounted with a securing plate 36 at a distance from the outer face 37 of the base plate 8 directed away from the inner face 9.

The flywheel disk 31 has a radially displaceable counterweight 38, which can be supplemented by an additional weight 39.

The invention claimed is:

1. An incubator (1) comprising:
   an incubation chamber (2) having a floor (6) with an opening (7);
   a device chamber (3) which adjoins the incubation chamber (2) at the floor (6); and
   a base plate (8) that extends across the opening (7) and seals off the incubation chamber (2) relative to the device chamber (3), the base plate (8) having an inner face (9) directed toward the incubation chamber (2) and an outer face (37) opposite the inner face (9);
   a motor (34) arranged on the outer face (37) of the base plate (8);
   a drive shaft (14) having a lower axle journal (30) that is in the device chamber (3) and is rotatably driven by the motor (34), an intermediate portion passing through the base plate (8) and an upper axle journals (20) in the incubation chamber (2), the upper axle journal (20) being arranged parallel to and offset from the lower axle journal (30); and
   a shaking table (11) in the incubation chamber (2) and mounted to the upper axle journal (20) for movement in a horizontal plane as the lower axle journal (30) is rotated by the motor (34), whereby the base plate (8) avoids moisture in the incubation chamber (2) from entering the device chamber (3) and limits heat flow from the device chamber (3) to the incubation chamber (2).

2. The incubator of claim 1, further comprising a fly wheel disk (31) on an end of the drive shaft (14) in the device chamber (3), the flywheel disk (31) being driven by the motor (34).

3. The incubator of claim 2, wherein the flywheel disk (31) is arranged centrally on the lower axle journal (30) and is connected by a drive belt (32) to a drive wheel (33) of the motor (34).

4. The incubator of claim 3, further comprising a radially displaceable counterweight (38) arranged on the flywheel disk (31).

5. The incubator of claim 1, wherein the drive arm (10) has at least one radially protruding end mounted on the base plate (8) via an eccentric rotary joint (16).

6. The incubator of claim 5, wherein the eccentric rotary joint (16) has an elastic damping member (27).

7. The incubator of claim 6, wherein the eccentric rotary joint (16) has a lower joint part (24) mounted rotatably on the base plate (8) via a lower joint pin (25) and is connected, via the elastic damping member (27), to an upper joint part (28), which has an upper joint pin (29) mounted rotatably in the drive arm (10).

8. The incubator of claim 7, wherein the upper joint pin (29) can be secured on the upper joint part (28) at at least two different distances from the longitudinal axis (40) of the lower joint pin (25).

9. The incubator of claim 1, wherein the drive shaft (14) is connected to the base plate (8) via bearings (17).

10. The incubator of claim 1, further comprising a seal (23) arranged between the drive shaft (14) and the base plate (8).

11. The incubator of claim 10, wherein the seal (23) is a low-friction lip seal or labyrinth seal.

* * * * *